US007162040B2

(12) United States Patent
Vanderveen

(10) Patent No.: US 7,162,040 B2
(45) Date of Patent: Jan. 9, 2007

(54) MOUNTING ASSEMBLY FOR ACTIVE NOISE ATTENUATION SYSTEM

(75) Inventor: James K. Vanderveen, Blenheim (CA)

(73) Assignee: Siemens VDO Automotive, Inc., Chatham (CA)

( * ) Notice: Subject to any disclaimer, the term of this patent is extended or adjusted under 35 U.S.C. 154(b) by 969 days.

(21) Appl. No.: 09/814,227

(22) Filed: Mar. 21, 2001

(65) Prior Publication Data

US 2002/0047074 A1 Apr. 25, 2002

Related U.S. Application Data

(60) Provisional application No. 60/193,225, filed on Mar. 30, 2000, provisional application No. 60/243,188, filed on Oct. 25, 2000.

(51) Int. Cl.
*A61F 11/06* (2006.01)
*F16M 13/00* (2006.01)

(52) U.S. Cl. ...................................... 381/71.5; 248/610

(58) Field of Classification Search ............... 381/71.1, 381/71.4, 71.5, 71.8, 71.9, 86, 71.7, 386, 381/365; 181/204, 724, 224–226
See application file for complete search history.

(56) References Cited

U.S. PATENT DOCUMENTS 4,638,965 A * 1/1987 De Bruine et al. ........... 248/59
5,647,314 A 7/1997 Mullins et al.
5,828,759 A * 10/1998 Everingham ................ 181/206
5,867,583 A * 2/1999 Hazelwood et al. ........ 381/395
6,005,957 A * 12/1999 Meeks ........................ 381/386
6,256,545 B1 * 7/2001 Kimura et al. ............. 381/71.4
6,505,705 B1 * 1/2003 Espiritu et al. ............. 181/150

FOREIGN PATENT DOCUMENTS

EP 0884471 A2 12/1998

OTHER PUBLICATIONS

Int'l Search Report, dated Jul. 15, 2002.

* cited by examiner

*Primary Examiner*—Laura A. Grier

(57) ABSTRACT

An active noise attenuation system includes a speaker housing for a speaker assembly that attenuates noise generated by an air induction system for a vehicle engine. The speaker housing is a generic housing formed from plastic that can be utilized with many different vehicle types. An air cleaner housing is positioned between the speaker housing and the engine for filtering out contaminants from the air before the air is drawn into the engine. Brackets are joined to the air cleaner and speaker housings for mounting the housings to a vehicle structure.

27 Claims, 2 Drawing Sheets

MOUNTING ASSEMBLY FOR ACTIVE NOISE ATTENUATION SYSTEM

RELATED APPLICATION

This application claims priority to provisional applications 60/193,225 filed on Mar. 30, 2000 and 60/243,188 filed on Oct. 25, 2000.

BACKGROUND OF THE INVENTION

1. Field of the Invention

This invention relates to a method and apparatus for mounting an active noise attenuation system in a vehicle.

2. Related Art

Internal combustion engines include air induction systems for conducting air to engine cylinders. Engine noise is propagated through the air induction systems, which is undesirable. Noise attenuation mechanisms have been installed within the air induction systems to reduce these noises. Typically these noise attenuation mechanisms include a speaker, a sound detector, a signal generator, and various other components that are used to reduce noise generated by the air induction system. These components are mounted within an air duct and speaker housing.

The housing is mounted to a vehicle structure such as the chassis with rubber grommets that provide additional isolation. The size and shape of the air duct and speaker housing varies dependent upon the vehicle type and application, which leads to part proliferation and increased costs. Additionally, automated assembly is difficult when different housing sizes are needed.

It is the object of the present invention to provide a simple and effective apparatus and method to mount an air duct and speaker housing that overcomes the deficiencies outlined above.

SUMMARY OF THE INVENTION

An active noise attenuation system is used to attenuate noise generated by an air induction system for a vehicle engine. In a disclosed embodiment of this invention, the active noise attenuation system utilizes a molded plastic speaker housing that is common to many vehicle types. Brackets are joined to the housing to mount the housing to a vehicle structure.

In one embodiment, an air cleaner housing is mounted between the speaker housing and the vehicle engine. At least one bracket is joined to each of the housings to mount the housings to a vehicle structure. The brackets can be joined to the housings in various manners including insert molding, welding, fastening, and snap fitting. An isolator is preferably mounted between each of the brackets and the vehicle structure to further reduce noise and vibration.

A method for mounting the active noise attenuation system to the vehicle structure includes the following steps. At least one bracket is joined to a generic speaker housing that is common to multiple vehicle types. The bracket is attached to a vehicle structure. Preferably, an air cleaner housing is positioned between the engine and the speaker housing and brackets are joined to the air cleaner housing and the speaker housing to mount the housing to the vehicle structure.

The subject apparatus provides a simple method for mounting an active noise attenuation system. As a result, a generic housing that is common to multiple vehicle types can be utilized, which deproliferates parts and reduces costs. Brackets are custom configured to mount the common housing within the vehicle.

These and other features of the present invention can be best understood from the following specification and drawings, the following of which is a brief description.

DETAILED DESCRIPTION OF AN EXEMPLARY EMBODIMENT

Figure 1:
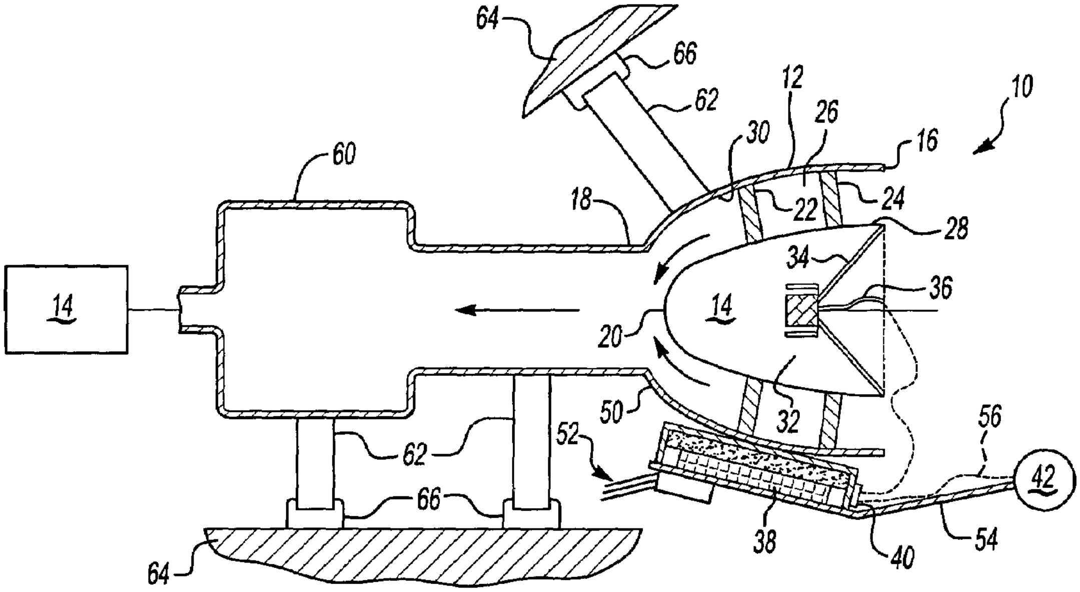
FIG. 1 is a schematic diagram of a noise attenuation system incorporating the subject invention.

Referring to the drawings, FIG. 1 shows a noise attenuation system 10 including a speaker housing 12 forming part of an air induction system for an internal combustion engine 14. The speaker housing 12 has an open forward facing end 16 and a rearward end 18 that faces the engine 14. The forward facing end 16 is of greater diameter than the rearward end 18.

Mounted within the speaker housing 12 is a mid-body portion 20. The mid-body portion 20 is concentrically positioned within speaker housing 12 on a pair of integrally formed struts 22, 24 to define an annular passage 26 between an exterior surface 28 of the mid-body portion 20 and an interior surface 30 of the speaker housing 12. The mid-body portion 20 is preferably parabola shaped to define a central chamber 32 with a tapered bottom end facing the engine 14 and an open end facing away from the engine 14.

A speaker assembly 34 is mounted within the chamber 32 and includes a speaker connector 36 that extends outwardly from the speaker assembly 34 towards the open forward facing end 16 of speaker housing 12. An electronics center 38 is operably connected to the speaker assembly 34 via a connector 40. The electronics center 38 can include a controller, microprocessor unit, or other similar device whose operation is well known in the art.

A sound detector 42, such as a microphone for example, is mounted within the air induction system to sense noise emanating from the engine 14. The sound detector 42 generates a noise signal that is sent to the electronics center 38 where the signal is phase-shifted by approximately 180 degrees. The phase-shifted signal is then sent to the speaker assembly 34 to generate a sound field that cancels out or attenuates the noise detected by the sound detector 42.

The electronics center 38 is mounted to an exterior surface 50 of the speaker housing 12 and includes a plurality of connections 52 for interfacing with various vehicle components.

The sound detector 42 is preferably mounted adjacent to the annular passage 26 in a forward position extending beyond the open forward facing end 16 of the speaker housing 12. The sound detector 42 can be supported on an arm 54 that mounts to the speaker housing 12 or electronics center 38. The arm 54 can be a separate piece or integrally formed with the housing 12 as one piece. A flex cable or flex circuit 56 preferably interconnects the sound detector 42 to the electronics center 38.

An air cleaner housing 60 is positioned between the engine 14 and the speaker housing 12. The air cleaner housing 60 houses a filtering mechanism (not shown) that removes contaminants from the airflow before the air enters the engine 14.

At least one bracket 62 is used to mount the speaker housing 12 and air cleaner housing 60 to a vehicle structural member such as the chassis 64. Preferably, a plurality of brackets 62 (see FIG. 1) are joined to the speaker 12 and air cleaner 60 housings by various methods, which will be discussed in detail below. Mounts 66 with isolators are positioned between each of the brackets 62 and the chassis 64 to further reduce noise and vibrations. Preferably rubber grommets are used, however, any type of isolator known in the art can be used. These mounts 66 will be discussed in further detail below.

Preferably, the speaker 12 and air cleaner 60 housings are generic housings molded from plastic that can be used for multiple vehicle types. This standardization of housings allows the housing to be produced in high volumes to reduce costs. The brackets 62 are custom made to mount the standard housings 12, 60 to the chassis 64.

Figure 2:
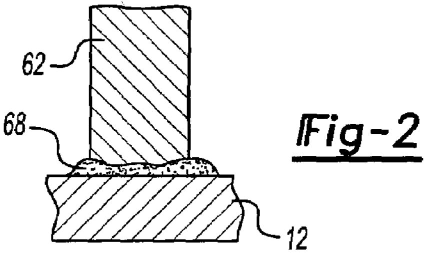
FIG. 2 shows one embodiment for attaching a bracket to a housing.
Figure 3:
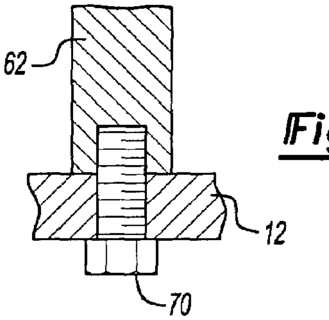
FIG. 3 shows another embodiment for attaching a bracket to a housing.
Figure 4:
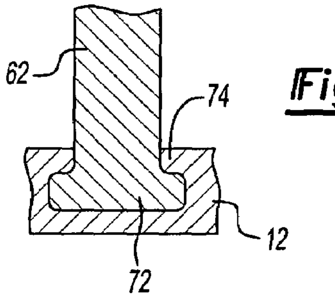
FIG. 4 shows another embodiment for attaching a bracket to a housing.

In one embodiment, shown in FIG. 2, the brackets 62 are welded at 68 to the housings 12, 60. In another embodiment, shown in FIG. 3, the brackets 62 are fastened to the housings 12, 60 with fasteners 70 (only one is shown). Various types of fasteners can be used including bolts, rivets, or screws. In another embodiment, the brackets 62 are pre-made and then insert molded within the housings 12, 60, see FIG. 4. The brackets 62 include a base portion 72 around which the housing 12 is molded at 74. The welding and insert molding methods are well known in the art and will not be discussed in detail.

Figure 5:
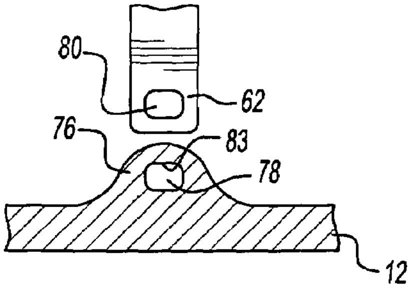
FIG. 5 shows another embodiment for attaching a bracket to a housing.
Figure 6:
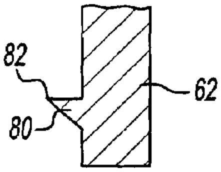
FIG. 6 is a side view of the bracket of FIG. 5.

Another joining method is illustrated in FIGS. 5 and 6. The bracket 62 is snap-fit into the housing 12. The housing 12 includes a lobe or ear extension 76 with an opening 78 that receives a resilient tab 80 formed on one end of the bracket 62. The tab 80 flexes as it is inserted into the opening 78 and rebounds such that a lip 82 engages an edge 83 of the opening 78 to retain the bracket 62 on the housing 12.

Figure 7:
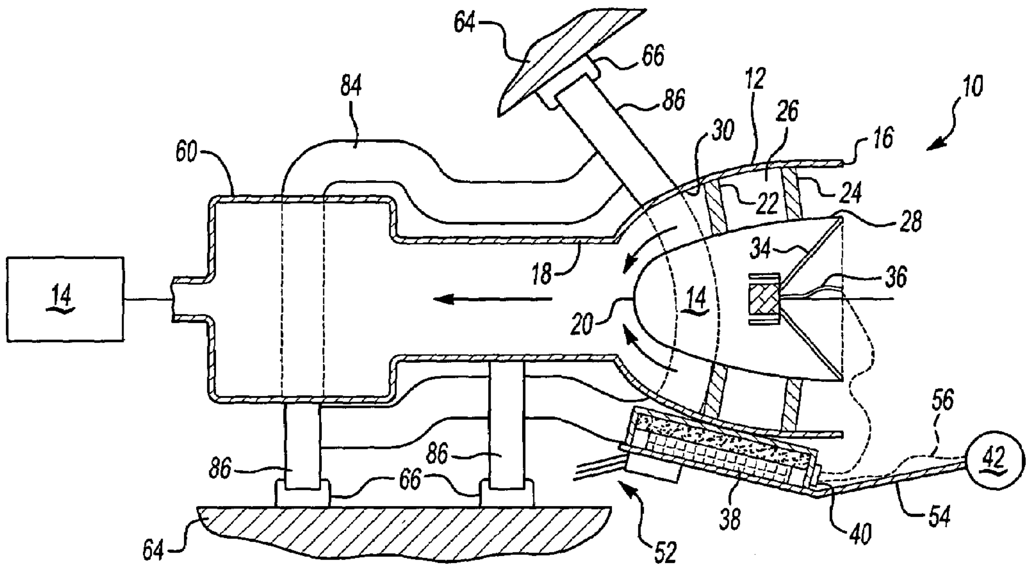
FIG. 7 is a schematic diagram of a noise attenuation system having an alternate bracket mount.

An alternate embodiment of a bracket mount is shown in FIG. 7. In this embodiment a single bracket body member 84 mounts the speaker housing 12 and air cleaner housing 60 to the chassis 64. The bracket body member 84 preferably includes at least three (3) leg portions 86 that extend from the body member 84 to the chassis 64. This provides a cradle mount for the speaker 12 and air cleaner 60 housings.

Figure 8:
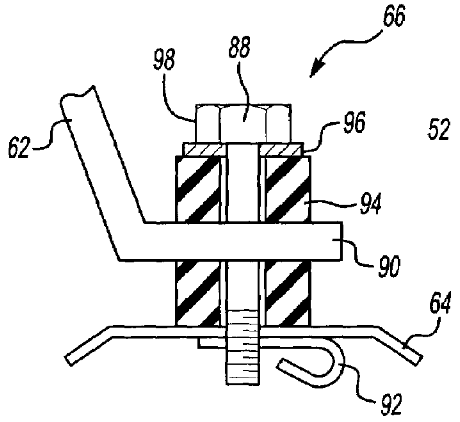
FIG. 8 shows a side view of a mount between the housing and vehicle structure.
Figure 9:
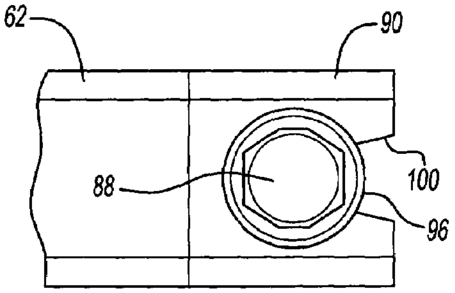
FIG. 9 is a plan view of the mount shown in FIG. 8.

The mounts 66 between the brackets 62 and the chassis are shown in greater detail in FIGS. 8 and 9. The mount 66 includes at least one fastener 88 that extends through a transverse distal portion 90 of the bracket 62 and into sheet metal of the chassis 64 or other vehicle structural member. A J-clip 92 or other similar member retains the fastener 88 to the sheet metal of the chassis 64. A rubber isomount 94 partially surrounds the fastener 88 to further reduce noise and vibrations. A metal insert 96 is positioned between the head 98 of the fastener and the isomount 94. The metal insert 96 serves as a torque limiter.

As shown in FIG. 9, the distal portion 90 of the bracket 62 includes a keyhole slot 100 for the mount 66. The mount 66 is slid through the slot 100 and fastened into place for easy and quick mounting.

The method for mounting the active noise attenuation system 10 to the chassis 64 includes the following steps. A generic speaker housing 12 is provided that is common to many different vehicle types. At least one bracket 62 is joined to the housing 12 and the bracket 62 is attached to the chassis 64. The housing is formed from plastic and the bracket 62 is joined to the housing 12 in any of various ways including pre-forming the bracket 62 and insert molding the bracket 62 to the housing 12, snap-fitting the bracket 62 to the housing 12, welding the bracket 62 to the housing 12, or fastening the bracket 62 to the housing 12. Preferably, an air cleaner housing 60 is positioned between the speaker housing 12 and the engine 14 and the brackets 62 are joined to both housings 12, 60, which are mounted to the chassis 64. Both housings can be generic housings that are made in high production volumes from molded plastic. The brackets 62 are custom made to account for mounting variations between vehicle types. The use of generic housings significantly reduces costs and provides a simplified interface for automated assembly methods.

Although a preferred embodiment of this invention has been disclosed, it should be understood that a worker of ordinary skill in the art would recognize many modifications come within the scope of this invention. For that reason, the following claims should be studied to determine the true scope and content of this invention.

What is claimed is:

1. An active noise attenuation system comprising:
- a plastic speaker housing having an open end into which air is drawn;
- a speaker mounted within said speaker housing;
- a plastic air cleaner housing positioned between said speaker housing and an engine; and
- a plurality of brackets joined to said speaker and air cleaner housings for attachment to a vehicle structure with at least one of said brackets mounting said air cleaner housing to the vehicle structure and at least one of said brackets mounting said speaker housing to the vehicle structure wherein each of said brackets includes a first end portion mounted to the vehicle structure and a distal portion joined with said air cleaner housing or said speaker housing.

2. A system according to claim 1 including an isolator mounted between said first and the vehicle structure.

3. A system according to claim 1 wherein said distal portions is welded to said housing.

4. A system according to claim 1 wherein said distal portions are fastened to said housings.

5. A system according to claim 1 wherein said distal portions are pre-formed and insert molded to said housing.

6. A system according to claim 1 wherein said distal portions are snap-fit to said housing.

7. A system according to claim 1 wherein said at plurality of bracket comprises a single bracket body having a plurality of leg mounts extending between said speaker and air cleaner housing and the vehicle structure.

8. A method for mounting an active noise attenuation system to a vehicle structure comprising the steps of:
- (a) providing a generic speaker housing common to multiple vehicle types;
- (b) forming the speaker housing as part of an air induction component having a passage for directing airflow to an engine;

(c) providing a bracket assembly including a plurality of bracket portions with each bracket portion having a first end portion and a distal portion;

(d) joining the distal portions to the speaker housing; and (e) attaching the first end portions to a vehicle structure.

9. A method according to claim 8 wherein step (b) includes forming the speaker housing from plastic.

10. A method according to claim 8 wherein step (d) includes pre-forming the bracket assembly and insert molding the distal portions to the speaker housing.

11. A method according to claim 8 wherein step (d) includes snap-fitting the distal portions to the speaker housing.

12. A method according to claim 8 wherein step (d) includes welding the distal portions to the speaker housing.

13. A method according to claim 8 wherein step (d) includes fastening the distal portions to the speaker housing.

14. A method for mounting an active noise attenuation system to a vehicle structure comprising the steps of:

(a) providing a generic speaker housing common to multiple vehicle types and an air cleaner housing positioned between the speaker housing and an engine;

(b) providing a bracket assembly including a plurality of bracket portions with each bracket portion having a first end portion and a distal portion;

(c) joining at least one distal portions to the air cleaner housing and joining at least one distal portion to the speaker housing; and (d) attaching the first end portions to a vehicle structure.

15. An active noise attenuation system comprising:

a first housing portion having an inlet into which air is drawn;

at least one noise attenuation component mounted within said first housing portion;

a second housing portion in fluid communication with said first housing portion for conducting air from said inlet into a vehicle engine wherein said first and second housing portions are molded from plastic; and a bracket assembly including a plurality of bracket portions with at least one of said bracket portions mounting said first housing portion to a vehicle structure and at least one of said bracket portions mounting said second housing portion to the vehicle structure wherein each of said bracket portions includes a first end portion mounted to the vehicle structure and a distal portion joined with said first or second housing portion.

16. A system according to claim 15 wherein said first housing portion comprises a speaker housing and said second housing portion comprises an air cleaner housing.

17. A system according to claim 15 including an isolator mounted between each of said bracket portions and the vehicle structure.

18. A system according to claim 15 wherein each of said distal portions is welded to said first or second housing portions.

19. A system according to claim 15 wherein each of said distal portions is fastened to said housing with at least one fastener.

20. A system according to claim 15 wherein said bracket assembly is pre-formed with one end of each of said distal portions being insert molded to one of said first or second housing portions.

21. A system according to claim 15 wherein each of said distal portions is snap-fit to said first or second housing portions.

22. A system according to claim 15 wherein said bracket assembly comprises a single bracket body member having a plurality of leg mounts that form said bracket portions, said leg mounts extending between said first and second housing portions and the vehicle structure to form a cradle mount.

23. A system according to claim 15 wherein said bracket assembly comprises a plurality of seperate bracket members with at least one of said bracket members mounting said first housing portion to the vehicle structure and at least one of said bracket members mounting said second housing portion to the vehicle structure.

24. A method according to claim 8 including the step of mounting an isolator between the first end portions and the vehicle structure.

25. A method for mounting an active noise attenuation system to a vehicle structure comprising the steps of:

(a) providing a generic speaker housing common to multiple vehicle types wherein the speaker housing includes an air cleaner housing portion adjacent to the speaker housing;

(b) providing a bracket assembly including a plurality of bracket portions with each bracket portion having a fist end portion and a distal portion;

(c) joining at least one of the distal portions to the speaker housing and joining at least one of the distal portions to the air cleaner housing portion; and (d) attaching the first end portions to a vehicle structure.

26. A method according to claim 8 including positioning an air cleaner housing between the speaker housing and the engine such that air flows through the passage from the speaker housing and into the air cleaner housing.

27. A method according to claim 26 including joining at least one distal portion to the speaker housing and at least one distal portion to the air cleaner housing.

* * * * *